United States Patent [19]

Sebag

[11] Patent Number: 5,182,407
[45] Date of Patent: Jan. 26, 1993

[54] SOLUBILIZING AND/OR DISPERSANT COMPOUNDS, PREPARATION PROCESS AND COMPOSITIONS CONTAINING THEM

[75] Inventor: Henri Sebag, Paris, France

[73] Assignee: L'Oreal, France

[21] Appl. No.: 731,441

[22] Filed: Jul. 17, 1991

[30] Foreign Application Priority Data

Jul. 25, 1990 [FR] France .................. 90 09532

[51] Int. Cl.$^5$ .............. C09F 5/00; C09F 7/00; C07C 317/14
[52] U.S. Cl. .................. 554/52; 554/38; 554/42; 554/59; 554/63; 562/430; 562/431; 562/556; 562/426; 514/852; 514/859; 514/880
[58] Field of Search ............ 554/38, 42, 52, 59, 554/63; 562/430, 431, 556, 436

[56] References Cited

U.S. PATENT DOCUMENTS 4,098,811 7/1978 Falk ..................... 554/38
4,242,516 12/1980 Mueller ................. 554/38

FOREIGN PATENT DOCUMENTS 0071993 2/1983 European Pat. Off. .

*Primary Examiner*—Johann Richter
*Attorney, Agent, or Firm*—Brumbaugh, Graves, Donohue & Raymond

[57] ABSTRACT

The present invention relates to the compounds of formula (I):

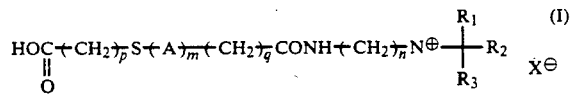

in which:
  $R_1$ and $R_2$, which are identical or different, denote a methyl or ethyl radical;
  $R_3$ denotes a methyl, ethyl or hydroxyethyl radical;
  A denotes a $$-CH_2-\underset{\underset{R}{|}}{CH}-$$

radical or

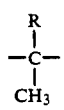

R denotes H or $CH_3$;
X denotes $Cl^-$, $BR^-$, $I^-$, $CH_3OSO_3^-$, $CH_3SO_3^-$,

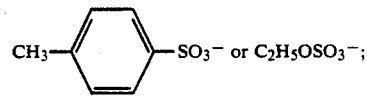

p and q, which are identical or different, denote integers such that $1 \leq p \leq 15$, $0 \leq q \leq 13$ and $2 \leq p+q \leq 20$;
n denotes an integer equal to 2 or 3;
m denotes 0 or 1, and $m+q \neq 0$;
as well as the salts from neutralization by bases, their preparation process and their utilization as an additive in compositions for treatment of keratinous materials.

7 Claims, No Drawings

SOLUBILIZING AND/OR DISPERSANT COMPOUNDS, PREPARATION PROCESS AND COMPOSITIONS CONTAINING THEM

The present invention relates to quaternary surfactant compounds, their preparation process and cosmetic and dermopharmaceutical compositions containing them.

In aqueous or aqueous-alcoholic cosmetic and dermopharmaceutical compositions, it is often necessary to use solubilising agents for products insoluble in water and it is known in this respect to use quaternary ammonium salts. The known quaternary ammonium salts can present certain drawbacks, especially at the level of their cutaneous tolerance.

The applicant has discovered novel quaternary surfactant compounds having good solubilising or dispersant properties in aqueous and aqueous-alcoholic media and presenting in an altogether surprising manner a very distinct improvement in properties at the level of cutaneous tolerance compared to known quaternary ammonium compounds.

An object of the invention is therefore aliphatic chain quaternary surfactant compounds comprising a carboxylic group, in the ω position with respect to the ammonium group, at the other end of the aliphatic chain.

Another object of the invention is a preparation process for the novel quaternary surfactant compounds.

In addition, the invention relates to compositions for treating keratinous material, intended for topical application and containing the quaternary surfactants according to the invention, as well as the use of these quaternary surfactants in an appropriate carrier for the cosmetic or dermopharmaceutical treatment of keratinous materials.

Other objects of the invention will become evident from reading the description and the examples which follow.

The compounds according to the invention are the quaternary surfactants represented by the general formula (I):

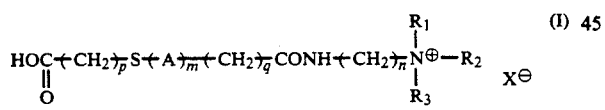

in which:

$R_1$ and $R_2$, which are identical or different, denote a methyl or ethyl radical;

$R_3$ denotes a methyl, ethyl or hydroxyethyl radical;

A denotes a

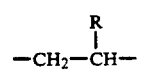

radical or

R denotes a hydrogen or a methyl radical;

$X^-$ denotes $Cl^-$, $Br^-$, $I^-$, $CH_3OSO_3^-$, $CH_3SO_3^-$,

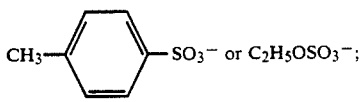

p and q, which are identical or different, denote integers such that $\leq p \leq 15$, $0 \leq q \leq 13$ and $2 \leq p+q \leq 20$;

n denotes an integer equal to 2 or 3;

m denotes 0 or 1, and $m+q \neq 0$;

as well as the salts from neutralisation by bases.

The bases for neutralisation of the carboxyl group, preferably cosmetically or pharmaceutically acceptable, can especially be chosen from amongst sodium hydroxide, potassium hydroxide, ammonia, magnesium hydroxide, dimethylethanolamine, the aminomethylpropanols, the aminomethylpropanediols, especially 2-amino-2-methylpropanol and 2-amino-2-methyl-1,3-propanediol, triethanolamine and N-methylglucamine.

The preferred compounds corresponding to the formula (I) are those for which $R_1$ and/or $R_2$ represent the methyl radical.

Other preferred compounds of formula (I) are those for which n represents 3, q represents 10 and m represents 0.

Particularly preferred compounds are 10''-carboxy-11'-decylthio-3-undecanoylaminopropyltrimethylammonium methylsulphate and 11'-carboxymethylthio-3-undecanoylaminopropyltrimethylammonium methylsulphate.

Another object of the invention comprises the process for preparation of carboxylic quaternary surfactants according to the invention.

They can be prepared starting from mercapto acids of formula (II):

$$HOOC-(CH_2)_p-SH \qquad (II)$$

by addition reaction with unsaturated derivatives of formula (III):

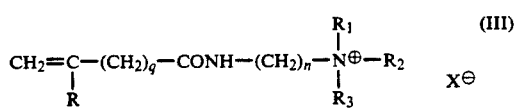

in which $R_1$, $R_2$, $R_3$, R, $X^-$, n, p and q have the same meanings as above, if appropriate in the presence of catalyst in an appropriate solvent.

By the customary exercise of choosing an appropriate solvent and reaction conditions, the addition can be directed to one or the other of the two carbons of the unsaturated bond.

In the case where R represents a methyl radical, a particularly preferred compound of formula (III) is 2'-methyl-3-propenoylaminopropyltrimethylammonium chloride, of formula:

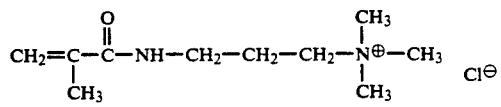

of which the corresponding amine is commercially available.

The addition reaction can be of the radical type, it then takes place in solvent medium in the presence of a free radical initiator.

As radical initiators, hydroperoxides can especially be mentioned such as tertiary butyl hydroperoxide, peroxides such as dibenzoyl peroxide, peresters such as tertiary butyl peroxybenzoate or the azo derivatives, and in particular azobisisobutyronitrile. The majority of solvents can be used, especially ethanol, toluene or tetrahydrofuran.

The quaternary ammonium compound of formula (III) is dissolved in the solvent in the presence of a radical initiator, then an approximately equimolar quantity of a mercapto acid of formula (II) is introduced, the reaction preferably being carried out under an inert atmosphere.

The addition reaction can also be carried out ionically in basic medium. In this case, isomers resulting from addition to one or the other ethylenic carbon are obtained.

The compounds of formula (I) where m is equal to 0 can likewise be obtained by condensation reaction of the same mercapto acids of formula (II) with halogenated derivatives of formula (IV):

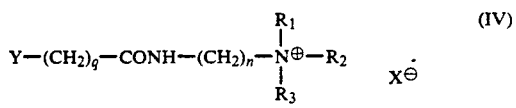

in which $R_1$, $R_2$, $R_3$, $X^-$, n, p and q have the same meanings as above and Y denotes Cl or Br, preferably Br.

The mercapto acids of formula (II) can be prepared starting from the homologous acid unsaturated at the end of the chain by reaction with thioacetic acid, as will be evident in the examples for the particular case where p represents 10.

Whatever the variant used for synthesising the quaternary surfactants according to the invention may be, the addition or condensation reaction can be followed by complete or partial neutralisation by one or more bases, especially chosen from among the group mentioned above.

The compounds of formula (I) are generally present in the form of white powders, soluble in water at room temperature, or giving nacreous solutions which clarify on becoming lukewarm.

The solubility and viscosity properties vary especially according to the values of p and q and as a function of the pH and of the base optionally used to neutralise the carboxyl group.

The compounds of the invention have very good dispersant and/or solubilising properties in aqueous medium for products which are insoluble or poorly soluble in aqueous or aqueous-alcoholic media. For this reason, the subject of the invention is the use of compounds of formula (I) as solubilisers and/or dispersants in aqueous or aqueous-alcoholic compositions. These poorly soluble or insoluble products can be, for example, hair colorants, waxes, polymers, active cosmetic or dermopharmaceutical agents, especially if they are of basic character. This will be evident in the examples below.

The compounds of the invention moreover have good cosmetic properties. In fact, they allow, for example, softness to be given, in particular to hair, which then facilitates its disentangling. They can thus be used for their softening properties.

Having taken into account their solubilising or dispersant properties in water for products which are generally difficult to formulate, their cosmetic properties and their excellent toxicological properties, the quaternary surfactants according to the invention are particularly of interest as additives in compositions for topical application and especially in compositions for treating keratinous material. Keratinous material according to the invention is understood to mean hair, nails and skin.

The invention therefore likewise relates to the use of the quaternary surfactants of formula (I) as additives in compositions for treating keratinous material.

The acid form of the compounds of formula (I) is most frequently preferred. It is nevertheless frequent to use in the same composition the compounds (I) and their salts from neutralisation by bases, especially by the bases mentioned above which are used to adjust the pH of the compositions by at least partially neutralising the acidic carboxyl group.

The invention therefore relates to aqueous or aqueous-alcoholic composition with a view to their topical application, characterised in that they comprise at least one compound of formula (I) according to the invention, or their salts from neutralisation with bases.

The compositions according to the invention contain from 0.1 to 10% by weight of compounds of formula (I), and preferably from 0.3 to 5% by weight.

The compounds according to the invention can be used for the transitory or semi-permanent coloration of the hair, for make-up or the removal of make-up, for the treatment of the hair with a view to improving disentangling or hair setting, for the preventative or curative treatment of dandruff, for the regrowth of hair or for preventing its loss, and for the treatment of the skin with a view to combating acne or any other infectious disease.

According to their use in cosmetics or in dermopharmacy, in addition to quaternary surfactant products of formula (I), or their salts, the compositions according to the invention can additionally contain active agents in an appropriate excipient.

Thus, in order to be appropriate for topical application, they can comprise water, a mixture of water with one or more organic solvent(s) and/or with one or more cosmetically and dermopharmaceutically acceptable fatty substances.

The compositions according to the invention can especially be present in the form of a solution, dispersion, milk, cream, foam, gel, cake or soap as well as in the form of a spray.

These compositions can optionally be pressurised in aerosol devices, in the presence of a propellant, optionally in the presence of foam generators or emulsifying agents.

As propellants, agents of the Freon, $C_3$ to $C_5$ alkane, methylene chloride or dimethyl ether type can be considered.

The solvents which can be used are chosen from among the $C_2$ to $C_5$ lower alcohols, such as ethyl alcohol or isopropyl alcohol, the glycol ethers, among which can be mentioned the monoethylene glycol monoalkyl ethers, the dialkylene glycol monoalkyl ethers and the triethylene glycol monoalkyl ethers, in which the alkyl group preferably has 1 to 4 carbon atoms, such as, for example, ethylene glycol monoethyl ether, ethylene glycol monobutyl ether and diethylene glycol monoethyl ether.

The compositions according to the invention can additionally contain one or more mineral, animal, vegetable or synthetic oils, in particular silicone oils, one or more ionic or non-ionic synthetic polymers, one or more polymers of natural origin, cellulosic polymers or polymers derived from chitin or chitosan.

The appropriate medium for topical application may or may not be thickened. In order to thicken it, thickening or gelling agents well known in the prior art can be used, such as, for example, guar gum, heterobiopolysaccharides, such as xanthan gum and scleroglucans, cellulose derivatives, such as methylcellulose, hydroxyethylcellulose, hydroxypropylmethylcellulose, the sodium salts of carboxymethylcellulose and preferably cross-linked acrylic acid polymers.

Other ionic or non-ionic surfactants, foaming or emulsifying agents can likewise be used.

As active agents, the compositions according to the invention can especially contain colorants customary for keratinous materials, sunscreens, preservatives, active agents for the regrowth of hair or for preventing its loss, like minoxidil, active agents for the treatment of dandruff, and active agents for the treatment of acne.

In addition, the compositions according to the invention can contain pearlisers or hydrating agents and preservatives or pH regulators, such as acids, bases, mineral salts or sterols.

The invention additionally relates to the use of compositions such as those defined above for the cosmetic treatment of keratinous materials and especially of the hair, nails or skin.

The following examples are intended to illustrate the invention without in any way having a limiting character.

PREPARATION OF COMPOUND A

10''-Carboxy-11'-decylthio-3-undecanoylaminopropyltrimethylammonium methylsulphate (A).

I. Preparation of 11-Mercaptoundecanoic Acid a) Procedure
The synthesis shown schematically below is carried out:

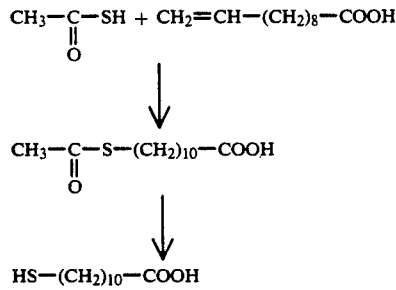

92 g of undecanoic acid (100% pure, "Fluka")
1.3 g of azobisisobutyronitrile (97% pure, "Fluka")
are introduced into a reactor.

The reactor is carefully purged with nitrogen and heated to 60° C. 30 g of thioacetic acid are steadily introduced in the course of 75 minutes; the reaction is exothermic and the temperature reaches 70° C.

After the addition, the temperature is kept at 70° C. for a further 4 hours with stirring and under nitrogen.

A solution of 66.7 g of potassium hydroxide dissolved in 25 ml of water and 180 ml of 96% ethanol is added in the course of 10 minutes to the preceding reaction medium, reduced to 40° C. It is then heated to reaction medium, reduced to 40° C. It is then heated to reflux and kept at this temperature for 3 hours under a nitrogen atmosphere.

After heating has been stopped, the ethanol is removed by reducing the pressure in the reactor, then 100 ml of water are added.

A solution of 106 g of concentrated 35% hydrochloric acid in 100 g of water is added in the course of 30 minutes to the preceding solution, kept at 50° C.

The acid formed during neutralisation floats on the surface in oily form.

The mixture, still under a nitrogen atmosphere, is left stirring for 1 hour; after separation, the aqueous phase (acid) is removed, and the organic phase is washed three times at 60° C. with 150 ml of water, recovered and concentrated.

105 g of an oily product are obtained which solidifies at room temperature. The yield is 96%.

The purity is 87% (thiol determination).

b) Analyses of the Product Obtained
The product can be additionally purified by molecular distillation:

Melting point: 52.5° C.

| Elemental analysis: $C_{11}H_{22}O_2S$ M.W. = 218.4 | | | | |
| --- | --- | --- | --- | --- |
| | C | H | O | S |
| Theoretical | 60.55 | 10.09 | 14.68 | 14.68 |
| Found | 60.64 | 10.16 | 14.38 | 14.68 |

II.
10''-Carboxy-11'-Decylthio-3-Undecanoylaminopropyltrimethylammonium Methylsulphate (A)

a) Procedure
The synthesis shown schematically below is carried out:

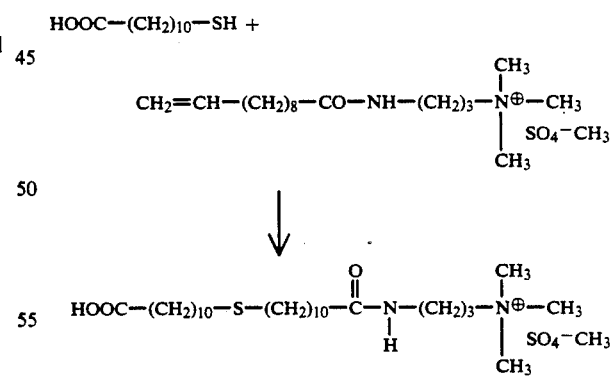

0.1 mol of 10'-undecen-3-oylaminopropyltrimethylammonium methylsulphate dissolved in water (47% active compound), i.e. 83.8 g of solution.
0.64 g of azobisisobutyronitrile
25 g of 96° ethanol
are introduced into a reactor carefully purged with nitrogen.

The 11-mercaptoundecanoic acid is used crude before distillation. Its thiol content is 86.7%. 10'-Undecen-3-oylaminopropyltrimethylammonium methylsulphate which is commercially available under the trademark "REWOCID UTM 185" marketed by REWO in approximately 50% solution in water is used at 47% active content.

The mixture is heated to 50° C.; 0.1 mol of pure, molten 11-mercaptoundecanoic acid, i.e. 25.1 g of 86.7% pure acid, is added in the course of 5 minutes to the clear solution, under a nitrogen atmosphere.

The mixture is then heated to 70° C. and kept at this temperature for 2 h 30 minutes with stirring and under nitrogen. The amount of reaction, determined by determination of the residual thiol, is then near to 95%.

0.16 g of azobisisobutyronitrile is added and heating is continued for 3 hours, while distilling the ethanol at normal pressure.

When reaction is complete, heating is stopped and removal of the solvents is continued by reducing the pressure in the reactor.

The residual reaction mixture is dissolved hot in 300 g of acetone.

The expected product recrystallises on cooling the filtered solution; it is dried and washed with cold acetone.

After drying, 56 g of white powder (yield=86.8%) are obtained.

b) Analyses of the Product Obtained
Melting point: 115° C.
13C-NMR: conforms to the formula.

| Elemental analysis: $C_{29}H_{60}N_2O_7S_2$ M.P. = 612 | | | | |
|---|---|---|---|---|
| C | H | O | N | S |
| Theoretical 56.86 | 9.81 | 18.30 | 4.57 | 10.46 |
| Found 56.72 | 9.84 | 18.26 | 4.51 | 10.36 |

PREPARATION OF COMPOUND B

11'-Carboxymethylthio-3-undecanoylaminopropyl-trimethyl-ammonium methylsulphate (B)

a) Procedure
The synthesis shown in schematic form below is carried out:

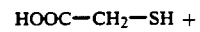

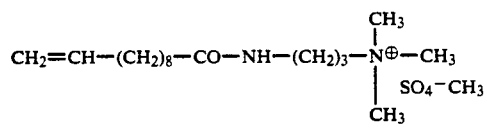

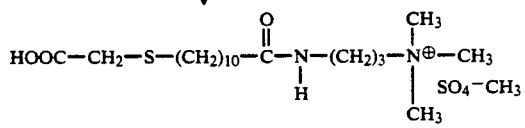

0.8 mol of 10'-undecen-3-oylaminopropyltrimethylammonium methylsulphate dissolved in water (47% of active compound), i.e. 670.6 g of solution.
3.9 g of azobisisobutyronitrile
220 g of 96% ethanol
are introduced into a reactor carefully purged with nitrogen.

The mercaptoacetic acid used is used at 97% active content. The 10'-undecen-3-oylaminopropyltrimethylammonium methylsulphate used is comparable to that used in Preparation Example A.

The mixture is heated to 55° C.; 0.8 mol of mercaptoacetic acid (97% of active compound), i.e. 75.9 g, is added in the course of 30 minutes to the clear solution under a nitrogen atmosphere.

The mixture is then heated to 65° C. and kept at this temperature for 3 h 30 minutes with stirring and under nitrogen. The amount of reaction, determined by determination of the residual thiol, is then near to 95%.

The temperature is increased to 80° C. and the solvents are distilled off in the course of 2 hours (200 g distilled off).

When reaction is complete, heating is stopped and removal of the solvents is continued by reducing the pressure in the reactor, in the same manner as in Example A.

The residual reaction mixture is dissolved hot in 2.5 l of acetone.

The expected product recrystallises on cooling the filtered solution; it is dried on a glass sinter and washed twice with cold acetone.

After drying, 300 g of white powder (yield=77%) are obtained.

b) Analyses of the Product Obtained
Melting point: 90° C.
13C-NMR: conforms to the formula.

| Elemental analysis: $C_{20}H_{42}N_2O_7S_2$ M.P. = 486 | | | | |
|---|---|---|---|---|
| C | H | O | N | S |
| Theoretical 49.38 | 8.64 | 23.05 | 5.76 | 13.17 |
| Found 49.48 | 8.68 | 22.90 | 5.79 | 13.11 |

FORMULATION EXAMPLES

EXAMPLE 1

A foam shampoo intended for hair regrowth treatment and of the following composition is prepared:

| | |
|---|---|
| minoxidil | 4.0 g |
| compound B | 9.7 g |
| non-ionic poly(hydroxypropyl) ether surfactant prepared by condensation, under alkaline catalysis, of 3.5 mol of glycidol with a mixture of alpha-diols having 11 to 14 carbon atoms, according to the procedure described in the Patent FR-2,091,516 | 13.0 g |
| preservatives qs | |
| water qsp | 100.0 g |

EXAMPLE 2

To prepare an aerosol packaging of the composition of Example 1, the following are used:

| | |
|---|---|
| composition of Example 1 | 95.0 g |
| ternary mixture of N-butane, isobutane >55% and propane, sold under the designation "AEROGAZ 3,2N" by ELF AQUITAINE | 5.0 g |

EXAMPLE 3

A non-rinse lotion intended for the treatment of regrowth of the hair and of the following composition is prepared:

|   |   |
|---|---|
| minoxidil | 2.0 g |
| compound B | 4.85 g |
| non-ionic poly(hydroxypropyl) ether) surfactant prepared by condensation, under alkaline catalysis, of 3.5 mol of glycidol with a mixture of alpha-diols having 11 to 14 carbon atoms, according to the procedure described in Patent FR-2,091,516 | 1.0 g |
| preservatives qs | |
| water qsp | 100.0 g |

EXAMPLE 4

A non-rinse gel intended for the treatment of regrowth of the hair and of the following composition is prepared:

|   |   |
|---|---|
| minoxidil | 3.0 g |
| compound A | 9.0 g |
| 95 vol % ethyl alcohol | 20.0 g |
| water qsp | 100.0 g |

EXAMPLE 5

The following colouring composition is prepared:

|   |   |
|---|---|
| compound A | 2.5 g |
| 1-N-(β-hydroxyethyl)amino-2-nitro-4-N',N'-(bis-β-hydroxyethyl)aminobenzene | 0.8 g |
| triethanolamine qs pH = 7 | |
| water qsp | 100.0 g |

EXAMPLE 6

The following hair colouring composition is prepared:

|   |   |
|---|---|
| compound B | 2.5 g |
| 1-N-(β-hydroxyethyl)amino-2-nitro-4-N',N'-(bis-β-hydroxyethyl)aminobenzene | 0.8 g |
| triethanolamine qs pH = 7 | |
| water qsp | 100.0 g |

EXAMPLE 7

The following hair colouring composition is prepared:

|   |   |
|---|---|
| compound A | 4.0 g |
| 1-N-(β-hydroxyethyl)aminobenzene N'-methyl-N'-(β-hydroxyethyl)aminobenzene | 0.6 g |
| triethanolamine qs pH = 7 | |
| water qsp | 100.0 g |

EXAMPLE 8

An antidandruff shampoo of the following composition is prepared:

|   |   |
|---|---|
| compound A | 0.6 g |
| sodium alkyl (C$_{12}$–C$_{14}$) ether sulphate oxyethylated with 2.2 mol of ethylene oxide, sold at 25% AM | 7.5 g |
| copra acid diethanolamide | 4.0 g |
| ethanolamine salt of 1-hydroxy-4-methyl-6-(2,4,4-trimethyl)pentyl-2-1H-pyridinone, sold under the designation "OCTOPYROX" by HOECHST | 0.2 g |
| colourings, perfume, qs | |
| triethanolamine qs pH = 7 | |
| water qsp | 100.0 g |

EXAMPLE 9

An after-shampoo rinse of the following composition is prepared:

|   |   |
|---|---|
| compound B | 0.5 g |
| hydroxyethylcellulose | 1.0 g |
| polymer of hydroxyethylcellulose and epichlorohydrin quaternised with trimethylamine, sold under the designation "JR 400" by UNION CARBIDE | 0.8 g |
| sodium chloride | 4.0 g |
| dialkyl (C$_{16}$-C$_{18}$/35–65) dimethylammonium chloride | 0.6 g |
| mixture (80/20) of cetylstearic alcohol and cetylstearic alcohol oxyethylated with 33 mol of ethylene oxide, sold under the name "SINNOWAX AO" by HENKEL | 2.0 g |
| stearyl alcohol | 1.0 g |
| cetyl alcohol | 1.0 g |
| preservatives, colourings, qs | |
| triethanolamine qs pH = 7 | |
| water qsp | 100.0 g |

EXAMPLE 10

Solubilisation of 1-N-(β-hydroxyethyl)amino-2-nitro-4-N',N'-(bis-β-hydroxyethyl)aminobenzene of formula:

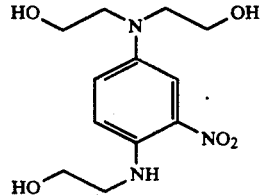

This colorant is insoluble in water at amounts of 0.8% by weight at pH7 set by triethanolamine.

The following composition is prepared:

|   |   |
|---|---|
| above colorant | 0.8% |
| compound A | 2.5% |
| triethanolamine qs pH = 7 | |
| water qsp | 100.0 g |

The colorant is solubilised.

Treatment of locks of hair:

A pair of locks of 90% white and 90% white permanent-waved hair (2×1.5 g) are immersed in 15 g of solution for 30 minutes. The hairs are then rinsed and dried.

|   | COLOUR |
|---|---|
| 90% WHITE HAIR | GREYISH PURPLE (0.7 RP; 3.9; 1.6) |
| 90% WHITE PERMED HAIR | BLACKISH PURPLE (4 P; 2.3; 3.3) |

The colour notation was carried out by the Munsell system, the three figures given respectively indicating the shade, the clarity and the saturation. The colorimetric measurements were carried out with the "Minolta CR 200".

EXAMPLE 11

The following composition is prepared under the same conditions as in Example 10:

| colorant from Example 10 | 0.8% |
|---|---|
| compound B | 2.5% |
| triethanolamine qs pH = 7 | |
| water qsp | 100.0 g |

The colorant 1 is solubilised under these conditions.
Treatment of locks of hair:
The results below were obtained using the same treatment protocol as in Example 10.

| | COLOUR |
|---|---|
| 90% WHITE HAIR | GREYISH PURPLE (1.1 RP; 3.9; 1.8) |
| 90% WHITE PERMED HAIR | BLACKISH PURPLE (4 P; 2.2; 3.4) |

EXAMPLE 12

Solubilisation of 3-nitro-4-N',
β-hydroxyethylamino-N-methyl-N-β-hydroxyethylaniline of formula

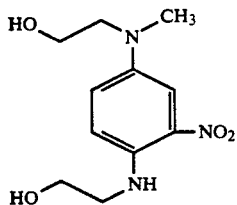

This colorant is insoluble in water at 0.6% by weight at pH7 set by triethanolamine.
Solubilisation thereof is carried out by preparing the following composition:

| above colorant | 0.6% |
|---|---|
| compound A | 4.0% |
| triethanolamine qs pH = 7 | |
| water qsp | 100.0 g |

Treatment of locks of hair:
The following results are obtained using the same treatment protocol as in Example 10:

| | COLOUR |
|---|---|
| 90% WHITE HAIR | DEEP GREYISH PURPLE (0.1 RP; 3.3; 2.6) |
| 90% WHITE PERMED HAIR | BLACKISH PURPLE (5.3 P; 2.1; 3.4) |

I claim:
1. Compounds of general formula (I):

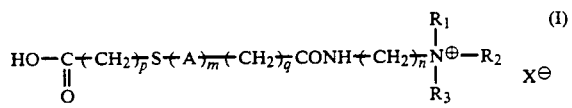

in which:
$R_1$ and $R_2$, which are identical or different, denote a methyl or ethyl radical;
$R_3$ denotes a methyl, ethyl or hydroxyethyl radical;
A denotes a

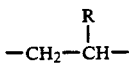

radical or

R denotes a hydrogen atom or a methyl radical;
$X^-$ denotes $Cl^-$, $Br^-$, $I^-$, $CH_3OSO_3^-$, $CH_3SO_3^-$,

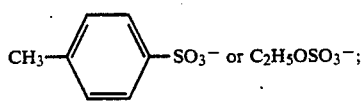

p and q, which are identical or different, denote integers such that $1 \leq p \leq 15$, $0 \leq q \leq 13$ and $2 \leq p+q \leq 20$;
n denotes an integer equal to 2 or 3;
m denotes 0 or 1, and $m+q \neq 0$;
as well as their salts from neutralisation by bases.

2. Compounds according to claim 1, characterised in that, in formula (I), $R_1$ and/or $R_2$ denote a methyl radical.

3. Compounds according to claim 1 or 2, characterised in that p=1 or 10, q=10, m=0, n=3, $R_1$, $R_2$ and $R_3$ denote a methyl radical and $X^-$ denotes $CH_3OSO_3^-$.

4. Compounds according to one of claims 1 or 2, characterised in that the bases for neutralisation are chosen from the group consisting of sodium hydroxide, potassium hydroxide, ammonia, magnesium hydroxide, dimethylethanolamine, aminomethylpropanols, aminomethylpropanediols, triethanolamine and N-methylglucamine.

5. A method for cosmetic and dermopharmaceutical treatment of keratinous materials, comprising applying to the keratinous materials a composition comprising as an active ingredient compounds selected from the group consisting of:
(a) compounds of the formula

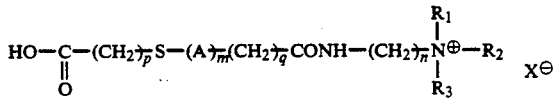

wherein
$R_1$ and $R_2$, which are identical or different, denote a methyl or ethyl radical;
$R_3$ denotes a methyl, ethyl or hydroxyethyl radical;

A denotes a

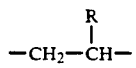

radical or

R denotes a hydrogen atom or a methyl radical;
X⁻ denotes Cl⁻, Br⁻, I⁻, CH₃OSO₃⁻, CH₃SO₃⁻, CH₃— —SO₃⁻ or C₂H₅OSO₃⁻;
p and q, which are identical or different, denote integers such that $1 \leq p \leq 15$, $0 \leq q \leq 13$ and $2 \leq p+q \leq 20$;
n denotes an integer equal to 2 or 3;
m denotes 0 or 1, and $m+q \neq 0$; and
(b) salts of such compounds obtained from neutralization by bases.

6. A method for solubilizing or dispersing aqueous and aqueous-alcoholic solutions, comprising adding to the aqueous or aqueous-alcoholic solution an effective amount of compounds selected from the group consisting of:
(a) compounds of the formula

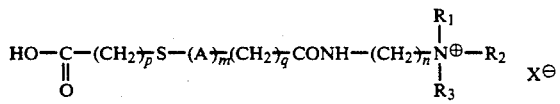

in which:
R₁ and R₂, which are identical or different, denote a methyl or ethyl radical;
R₃ denotes a methyl, ethyl or hydroxyethyl radical;
A denotes a

radical or

R denotes a hydrogen atom or a methyl radical;
X⁻ denotes Cl⁻, Br⁻, I⁻, CH₃OSO₃⁻, CH₃SO₃⁻, CH₃— —SO₃⁻ or C₂H₅OSO₃⁻;
p and q, which are identical or different, denote integers such that $1 \leq p \leq 15$, $0 \leq q \leq 13$ and $2 \leq p+q \leq 20$;
n denotes an integer equal to 2 or 3;
m denotes 0 or 1, and $m+q \neq 0$; and
(b) salts of such compounds obtained from neutralization by bases.

7. A method for cosmetic treatment of hair, nails or skin, comprising the step of applying to the hair, nails or skin a composition selected from the group consisting of an aqueous composition and an aqueous-alcoholic composition, wherein the compositions further comprise as an active ingredient compounds selected from the group consisting of:
(a) at least one compound of formula

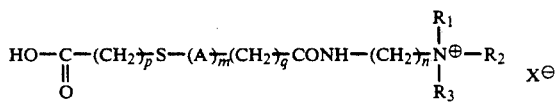

in which:
R₁ and R₂, which are identical or different, denote a methyl or ethyl radical;
R₃ denotes a methyl, ethyl or hydroxyethyl radical;
A denotes a

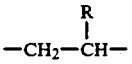

radical or

R denotes a hydrogen atom or a methyl radical;
X⁻ denotes Cl⁻, Br⁻, I⁻, CH₃OSO₃⁻, CH₃SO₃⁻, CH₃— —SO₃⁻ or C₂H₅OSO₃⁻;
p and q, which are identical or different, denote integers such that $1 \leq p \leq 15$, $0 \leq q \leq 13$ and $2 \leq p+q \leq 20$;
n denotes an integer equal to 2 or 3;
m denotes 0 or 1, and $m+q \neq 0$; and
(b) salts of such compounds obtained from neutralization by bases.

* * * * *

UNITED STATES PATENT AND TRADEMARK OFFICE
CERTIFICATE OF CORRECTION

PATENT NO. : 5,182,407

DATED : January 26, 1993

INVENTOR(S) : Henri Sebag

It is certified that error appears in the above-identified patent and that said Letters Patent is hereby corrected as shown below:

Column 4, line 24, "composition" should read --compositions--;

Column 9, line 52, "1-N-(ß-hydroxyethyl)aminobenzene" should read --1-N-(ß-hydroxyethyl)amino-2-nitro-4- --;

Column 13, line 16, "CH-$_3$- -SO$_3$-" should read --  --;

Column 13, line 24, "dispersing" should read --dispersing insoluble products in--;

Signed and Sealed this

Twenty-eighth Day of December, 1993

Attest:

BRUCE LEHMAN

Attesting Officer Commissioner of Patents and Trademarks

UNITED STATES PATENT AND TRADEMARK OFFICE
CERTIFICATE OF CORRECTION

PATENT NO. : 5,182,407

DATED : January 26, 1993

INVENTOR(S) : Henri Segag

It is certified that error appears in the above-identified patent and that said Letters Patent is hereby corrected as shown below:

<u>Column 14, line 3,</u>   "CH$_3$- -SO$_3$-" should read
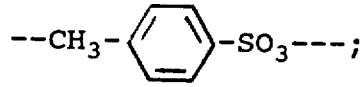

<u>Column 14, line 44,</u>  "CH$_3$- -SO$_3$-" should read
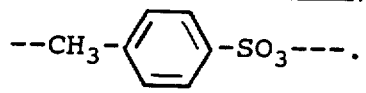

Signed and Sealed this

Seventh Day of June, 1994

Attest:

BRUCE LEHMAN

Attesting Officer          Commissioner of Patents and Trademarks